United States Patent [19]

Pichierri

[11] Patent Number: 5,194,261
[45] Date of Patent: Mar. 16, 1993

[54] DIAPER RASH TREATMENT

[76] Inventor: Virgil Pichierri, 50 Brigham Hill Rd., Grafton, Mass. 01519

[21] Appl. No.: 879,533

[22] Filed: May 4, 1992

Related U.S. Application Data

[63] Continuation of Ser. No. 618,395, Nov. 27, 1990, abandoned.

[51] Int. Cl.$^5$ .............................................. A61K 7/40
[52] U.S. Cl. .................................. 424/401; 424/78.2; 424/78.06; 424/494; 514/865
[58] Field of Search ................... 424/78, 401, 49, 448, 424/484, 488, 494, 78.06, 78.2, 78.33; 604/360; 514/865; 524/17, 22, 45, 55

[56] References Cited

U.S. PATENT DOCUMENTS

| | | | |
|---|---|---|---|
| 3,876,771 | 4/1975 | Denner | 424/78 |
| 4,382,919 | 5/1983 | Alonso et al. | 424/78 X |
| 4,556,560 | 12/1985 | Buckingham | 514/865 |
| 4,728,642 | 3/1988 | Pawelchak et al. | 514/59 X |
| 4,816,254 | 3/1989 | Moss | 514/865 |
| 4,857,321 | 8/1989 | Thomas | 514/865 |
| 4,996,238 | 2/1991 | Matravers | 514/865 |

Primary Examiner—Thurman K. Page
Assistant Examiner—D. Colucci
Attorney, Agent, or Firm—David H. Judson

[57] ABSTRACT

An improved method of treating diaper rash in both infants and adults is described. The method entails coating the affected area with a composition containing a copolymer of a lower alkyl vinyl ether and maleic acid, or a derivative of the copolymer.

11 Claims, No Drawings

DIAPER RASH TREATMENT

This is a continuation of copending application Ser. No. 07/618,395 filed on Nov. 27, 1990, now abandoned.

BACKGROUND OF THE INVENTION

Diaper rash is an inflammation of the skin in the diaper area of neonates, infants, children, and incontinent adults. It is generally believed caused by the metabolic by-products of both urine and feces. Currently available treatments for diaper rash are generally based upon the use of zinc oxide, vitamins (A, D, and $D_3$), or some combination thereof. These active ingredients are incorporated into a cream or salve by blending them into various purified semisolid ointment bases, e.g. mineral oil, petrolatum, soft paraffin, lanolin, and the like. While these treatments are oftentimes effective for treating routine, simple diaper rashes, severe cases of diaper rash, especially those often observed with incontinent adults, have proved resistant to the treatments.

Accordingly, there is a need for an improved diaper rash treatment, particularly for use in severe cases.

The primary component of the compositions used herein for the improved treatment of diaper rash is a copolymer of a lower alkyl vinyl ether and maleic acid. U.S. Pat. Nos. 3,003,988 and 4,393,080 disclose the use of the copolymer and derivatives thereof as an adhesive for fixing dentures or ostomy devices to mucous membranes. U.S. Pat. No. 4,910,247 discloses a blend of a mixed salt of the copolymer in combination with a stearic acid metal salt as an improved adhesive for denture and ostomy use. U.S. Pat. No. 3,876,771 discloses a skin protection gel for use in protecting a stoma from fecal matter and still active gastric juices, which gel contains 25 to 95% isopropanol along with the monoisopropyl ester of the copolymer. U.S. Pat. No. 4,007,263 discloses a method of relieving irritation of skin (due to fecal drainage) surrounding an iliac stoma by applying thereto a composition containing at least 40% of a calcium, sodium partial mixed salt of the copolymer in a petroleum jelly base. U.S. Pat. No. 4,728,642 discloses a method of treating wounds by packing a wound emitting a large amount of fluid with granular material and then covering the wound site with an adhesive layer containing in part the copolymer or a derivative thereof. European Appln. 0,260,859 discloses a medicated skin composition containing the copolymer, isopropyl alcohol, citric acid ester plasticizer, and a specific antimicrobial agent.

Accordingly, the copolymer and its derivatives, while having been found to have utility as an adhesive, for protecting and relieving irritation from fecal matter (normally neutral or slightly alkaline) around a stoma, as part of an adhesive layer over a wound, and as a carrier/adhesive for an antimicrobial agent, has not been used as a treatment for diaper rash or to relieve skin irritation caused by contact with urine (normally slightly acidic), its metabolic by-products, infant feces (usually acidic), and its metabolic by-products.

It is thus an object of the present invention to produce a treatment for and inhibition of diaper rash in neonates, infants, children, and incontinent adults, which treatment is effective even in severe cases of diaper rash.

SUMMARY OF THE INVENTION

The present invention comprises treating a diaper rash in which urine and/or its metabolic by-products are the cause of or a contributing factor to the rash. More particularly, in one embodiment of the invention for the treatment of severe diaper rash the invention entails applying to a situs of the severe diaper rash a composition comprising about 15 to 40% of a copolymer, or derivative thereof, of a lower alkyl vinyl ether and maleic acid dispersed in a semisolid ointment base, over-coating the copolymer composition with a layer of a semisolid water-insoluble ointment base, and allowing the copolymer composition to remain essentially intact for an extended period of time, generally through several diaper changes. Healing of the skin is generally observed within about 1 to 4 days. The over-coating layer is removed and then reapplied with each successive diaper change. Periodically, e.g. daily, the copolymer composition is removed (if it comes off easily) to inspect the skin and reapplied. In an alternative embodiment of the invention for the treatment of minor diaper rash as well as to inhibit the development of diaper rash, the invention entails applying at each diaper change a coating to the skin in the diaper area of a composition comprising about 5 to 20% of a copolymer, or a derivative thereof, of a lower alkyl vinyl ether and maleic acid dispersed in a semisolid ointment base.

DETAILED DESCRIPTION OF THE INVENTION

The present diaper rash treatment utilizes a composition comprising a copolymer of a lower alkyl ($C_1$–$C_3$) vinyl ether and maleic acid, or a derivative thereof, dispersed in a semi-solid ointment base.

Suitable copolymers for use herein are commercially available from GAF Corporation, Wayne, N.J., and are currently sold under the trademark GANTREZ ®. The copolymers are preferably used in the form of a derivative thereof in which one or both of the acid groups have been converted to a metal salt or an alkyl ester. Suitable metal salts include such as calcium, sodium, and a mixture thereof. Suitable alkyl groups for the esters include propyl, isopropyl, butyl, isobutyl, and mixtures thereof. Generally about 20 to 90%, preferably about 70 to 90% for the metal salt and about 30 to 45% for the ester, of the initial carboxyl groups are reacted. The copolymers generally have a molecular weight of about 18,000 to 80,000 daltons (as measured by membrane osmometry in a 2-butanone 1–10 grams/1000 ml solution). The currently most preferred copolymer derivative is the mixed calcium and sodium salt blend supplied as GANTREZ ® MS-955 wherein the proportion of Ca:Na is about 5–6:1 and the molecular weight is about 65,000– 70,000. Other examples of specific copolymers useful herein include S-97 (intact acid groups), AN-169 (anhydride), ES-335 (monoisopropyl ester), ES-435 (monobutyl ester), and ES-425 (monobutyl ester).

The semisolid ointment base in which the copolymer is dispersed and which serves to prevent the copolymer from becoming too hard in use may be any such material conventionally used as a vehicle for medicinal substances for topical application. Suitable water-insoluble ointment bases for use herein include petrolatum, white petrolatum, lanolin, and the like. Suitable water-soluble ointment bases for use herein include polyethylene glycol polymers and the like. Preferably a water-insoluble ointment base is used because the water-soluble bases may in some instances be irritating to inflamed tissue as is present with a diaper rash.

Additional ingredients which may be present in the copolymer composition include oils such as mineral oil, fish liver oil, and cod liver oil; emollients such as glycerin, olive oil, and lanolin; fillers such as cellulose gum, calcium carbonate, karaya gum, gum tragacanth, gum acacia, carboxymethyl cellulose, and polyvinyl acetate; vitamins such as vitamins A, D, and $D_3$; astringents such as zinc oxide and aluminum acetate; protectants such as Peruvian balsam; coloring agents; odorants; and other materials which are conventionally used in relieving skin irritation.

Preferably the compositions used herein are alcohol-free since alcohol, which can be absorbed systemically, can be fatal to neonates and is likely to cause burning and be an irritant to previously irritated skin.

The viscosity of the compositions used herein has not been found to be critical, and thus the specific viscosity of the composition will be selected merely as a matter of convenience. Generally any conventional cream or ointment viscosity may be used with variations merely affecting the ease of application. Generally, however, compositions used for treatment of severe diaper rash will have a higher viscosity than those used for inhibiting and/or treating mild diaper rash.

Compositions particularly useful for treating severe cases of diaper rash, i.e. in which the skin is denuded, excoriated, ulcerated and/or severely inflamed, generally contain about 15 to about 40 weight percent of the copolymer, preferably about 20 to about 35 weight percent. The additional ingredients may be present in total amounts of up to about 50 weight percent, preferably up to about 30 weight percent. The balance of the composition is one or more semisolid ointment bases.

To utilize the compositions for severe diaper rash, they should be liberally applied over the specific irritation sites and then allowed to remain in place for an extended period of time, generally for several diaper changes. Healing generally has been noted to occur in about 1 to 4 days. To allow the treatment composition to remain in place for the extended period as well as to minimize any potential trauma and discomfort to the patient from repetitive removals of the composition and to prevent undue adherence to a diaper placed thereover, it has been found convenient to apply a coating of a semi-solid water-insoluble ointment base, e.g. petrolatum or lanolin, atop the treatment composition. The ointment base top coating can then be removed for cleaning purposes and then reapplied for successive rediaperings while allowing the treatment composition to remain essentially undisturbed. Periodically, e.g. daily, the treatment composition should be removed to inspect the skin and additional composition applied if healing is not complete. During the periodic replacement of the treatment composition, if it does not readily detach from the skin it should be allowed to remain in place for an additional period to prevent trauma to the patient. When healing is complete, or earlier, the treatment composition may be completely removed by the conventional use of soap and water.

Compositions particularly useful for inhibiting the development of diaper rash and for treating mild cases thereof, i.e. in which the skin is slightly red, sore, warm to the touch, and/or the commencement of inflamation is evident, generally contain about 5 to 20 weight percent of the copolymer, preferably about 8 to 15 weight percent. The additional ingredients may then be present in amounts of up to about 60 weight percent, preferably up to about 40 weight percent. The balance of the composition is one or more semisolid ointment bases.

To utilize the inhibiting and mild treatment compositions, they will generally be applied at a diaper change and then removed and reapplied at subsequent diaper changes in the same manner as other diaper rash products are currently utilized. If desired, an overcoating of a semi-solid water-insoluble ointment base may be applied atop the treatment composition.

During use of the copolymer compositions it is currently believed that the copolymer component becomes at least partially hydrated which causes it both to adhere to the skin and to form a firmly adhered barrier against diaper rash causative and irritant agents. While diaper rash is believed caused primarily by the metabolic by-products of wastes in general, there are acidic components of urine and infant stools which are not present in adult feces and are particularly irritating. Urine consists of approximately 93-97% water and 3-7% solids which include urea, uric acid (20 to 40 gm/day), creatine (methylglycocyamine; 0 to 40 mg/day in men and 0 to 80 mg/day in women), creatinine (1methylglycocyamidine; the end product of creatine metabolism; 15 to 25 mg/kg of body weight/day), ammonia (0.5 to 1.3 gm/ day), and inorganic substances such as chlorides, calcium, magnesium, and phosphorous. Urine is normally slightly acidic. Feces, on the other hand, of adults is normally neutral or slightly alkaline while that of infants is slightly acidic. It is the acidic agents which are believed to be highly irritating in the diaper area.

In the following non-limiting examples of diaper rash treating compositions and the use thereof, all parts and percents are by weight unless otherwise specified.

EXAMPLE I

An 8 month old congenital caridiac patient had had a continuing diaper rash for over 2 months. Various therapies, including antifungals were tried over this period without success.

Inspection of the skin indicated an underlying fungal infection as well as several areas of epidermal denudation. A single application of an antifungal powder, i.e. MYCOSTATIN, followed by a conventional skin sealant, i.e. Bard wipe, to hold the powder in place was applied to the perineum. A treatment composition was prepared by blending and uniformly mixing 30.75% GANTREZ®MS-955, 15.4% cellulose gum, 5% mineral oil, 0.0224% peppermint oil, 0.017% D+C Red #27 Lake, 0.01% D+C Red #30 Lake, and white petrolatum q.s.

The treatment composition was applied over the skin sealant and surrounding areas in an amount sufficient to form a coating about 1-2 mm thick. No pain or discomfort was experienced by the patient during the application of the treatment composition. The coating was then overcoated with a layer of petrolatum jelly and a diaper placed thereover. At each diaper change, only the white petrolatum overcoating was removed, the patient cleaned, and a fresh over-coating applied, i.e. the treatment composition remained intact.

Within two days, this chronic diaper rash had started to resolve. After 7 days no diaper rash inflammation was still visible and the treatment composition was removed by the liberal use of soap and water.

EXAMPLE II

The procedure of Example I was repeated with an 8 month old ventilator dependent boy with medically managed Hirschprungs disease who was bothered by occasional diarrhea. Several therapies had been tried without success when the treatment composition of Example I was directly applied to the diaper area of the patient, overcoated with a layer of petroleum jelly, and a diaper placed thereover. At each diaper change, only the white petrolatum overcoating was removed, the patient cleaned, and a fresh over-coating applied, i.e. the treatment composition remained intact.

Within only 24 hours considerable improvement of the diaper rash was readily apparent. After 2 days no diaper rash inflammation was still visible and the treatment composition was removed by the liberal use of soap and water.

EXAMPLE III

A 6 year old oncology patient developed intractable diarrhea during a course of chemotherapy. Both his energy level and mobility were diminished. His appetite was poor but he received optimal calories via parenteral nutrition. Because of his diminished level of activity he wore diapers. Despite preventative perianal care being administered using a protective moisture barrier cream of Carrington Company as well as numerous alternative conventional treatments and cleansing with each diaper change, severe perianal denudation occurred.

The perianal area was cleaned with a mild antibacterial soap and inspected for signs of underlying fungal infection. The skin appeared free from fungal infection. The treatment composition of Example I was applied to the denuded skin and covered with a layer of petroleum jelly as in Example I. After, each diaper change was performed by cleansing (while leaving the treatment composition intact) and reapplying the petroleum jelly.

Remarkable improvement in skin integrity was apparent after 24 hours and essentially complete healing was evident after 7 days.

EXAMPLE IV

To inhibit the recurrence of the diaper rash on the patient of Example I, the following composition is applied and then removed on subsequent diaper changes: 10% GANTREZ® MS-955, 12% cellulose gum, 21% mineral oil, 10% lanolin, 3% zinc oxide, 0.0224% peppermint oil, and white petrolatum q.s. No recurrence is noted during a 20 day observation period.

EXAMPLE V

The following compositions are prepared for treating severe diaper rash:

| Ingredient | A | B | C | D | E | F |
|---|---|---|---|---|---|---|
| Gantrez ® MS-955 | 25 | — | — | 10 | 15 | 20 |
| Gantrez ® S-97 | — | 35 | — | — | 15 | — |
| Gantrez ® ES-335 | — | — | 30 | — | — | 7 |
| Gantrez ® ES-435 | — | — | — | 20 | — | 8 |
| Mineral oil | — | — | 5 | 2 | — | 1 |
| Cod liver oil | 4 | — | — | 10 | — | 1 |
| Cellulose gum | — | 12 | 10 | 8 | 18 | 4 |
| Calcium carbonate | 16 | — | 10 | — | 12 | — |
| Karaya gum | — | 4 | — | 12 | — | — |
| Vitamin A | 2 | — | 12 | — | — | 5 |
| Vitamin D | 2 | — | 6 | — | — | 2 |
| Aluminum Acetate | — | 7 | — | 5 | — | 2 |
| Colorant | — | — | — | — | 0.01 | 0.02 |
| Odorant | — | — | — | 0.01 | — | — |
| White petrolatum | qs | — | qs | — | — | qs |
| Lanolin | 5 | — | — | 11 | 20 | 2 |
| Petrolatum | — | qs | — | qs | qs | — |

The compositions are used in Examples I–III for a variety of patients including neonates, infants, and adult incontinents. Similar results to those of the Examples are observed in each case.

EXAMPLE IV

The following compositions are prepared for regular use to inhibit diaper rash formatioin and to treat minor cases thereof:

| Ingredient | A | B | C | D | E | F |
|---|---|---|---|---|---|---|
| Gantrez ® MS-955 | 5 | — | 10 | — | 15 | — |
| Gantrez ® S-97 | 2 | 4 | — | 7 | 3 | 10 |
| Gantrez ® ES-335 | — | 1 | 6 | — | — | — |
| Gantrez ® ES-435 | 5 | — | — | 15 | — | — |
| Mineral oil | 15 | — | 20 | — | 5 | 10 |
| Cod liver oil | 7 | 10 | — | — | 15 | — |
| Cellulose gum | — | 10 | 15 | — | — | 20 |
| Karaya gum | 2 | — | — | 12 | — | — |
| Vitamin A | — | — | 10 | — | 15 | — |
| Vitamin D | — | 5 | — | 8 | — | 12 |
| Aluminum Acetate | 7 | — | 12 | — | 20 | — |
| Colorant | — | 0.01 | — | — | 0.05 | — |
| Odorant | 0.1 | — | 0.05 | — | — | — |
| White petrolatum | q.s. | — | q.s. | — | q.s. | — |
| Lanolin | 10 | — | 10 | — | 20 | 25 |
| Petrolatum | — | q.s. | — | q.s. | — | q.s. |

The compositions are used by application of a fresh coating with each diaper change to a group of 10 neonates. A second group of 10 neonates, used as a control, are washed thoroughly at each diaper change. After 10 days, the untreated neonates exhibit substantially increased incidence of diaper rash.

What is claimed is:

1. A method of treating a diaper rash which comprises:
    applying to an area of diaper rash a composition comprising about 10 to about 40% by weight of a copolymer of an alkyl vinyl ether, having about 1 to 3 carbon atoms in the alkyl group, and maleic acid, wherein about 20% to about 90% of acid groups of the maleic acid are reacted to convert them to a group selected from the group consisting of a metal salt and an alkyl ester having about 2 to 6 carbon atoms, the copolymer being dispersed in a topically-acceptable carrier, the copolymer capable of reacting with waste by-products during use to become partially hydrated to thereby adhere to the skin and to form a barrier against diaper rash causative and irritant agents;
    over-coating the composition with a layer consisting essentially of semi-solid ointment;
    wherein when the copolymer becomes partially hydrated the over-coat layer prevents the composition from substantially adhering to a diaper surface; and
    removing and reapplying the over-coat layer during successive diaper changes while allowing the composition underlying said layer to remain essentially undistributed throughout said successive diaper changes to thereby enable the skin to heal.

2. The method of claim 1, wherein the copolymer composition is removed after about one day and reapplied if healing is not complete.

3. The method of claim 1, wherein about 70 to 90% of the acid groups are converted to metal salts selected from the group consisting essentially of calcium, sodium, and mixtures thereof.

4. The method of claim 1, wherein about 30 to 45% of the acid groups are converted to alkyl esters wherein the alkyl group is selected from the group consisting of propyl, isopropyl, butyl, isobutyl, and mixtures thereof.

5. The method of claim 1, wherein the topically-acceptable carrier is selected from the group consisting essentially of petrolatum, white petrolatum, and lanolin.

6. The method of claim 1, wherein the over-coat layer is selected from the group consisting of petrolatum, white petrolatum, and lanolin.

7. The method of claim 1, wherein the composition further contains at least one additive selected from the group consisting of oils, emollients, fillers, vitamins, astringents, coloring agents, and odorants.

8. The method of claim 1, wherein the composition comprises about 20 to about 35% of the copolymer and derivatives thereof.

9. The method of claim 1, wherein the composition is alcohol-free.

10. A method of treating a diaper rash which comprises the steps of:

applying to an area of diaper rash a composition comprising about 10 to about 40% by weight of a calcium, sodium partial mixed salt of a copolymer of vinyl methyl ether and maleic acid dispersed in a topically-acceptable carrier, the copolymer capable of reacting with waste by-products during use to become partially hydrated to thereby adhere to the skin and to form a barrier against diaper rash causative and irritant agents;

over-coating the composition with a layer consisting essentially of semi-solid ointment;

wherein when the copolymer becomes partially hydrated the over-coat layer prevents the composition from substantially adhering to a diaper surface; and removing and reapplying the over-coat layer during successive diaper changes while allowing the composition underlying said layer to remain essentially undistributed throughout said successive diaper changes to thereby enable the skin to heal.

11. A composition suitable for use in treating a diaper rash, comprising:

about 30.75% of a calcium, sodium partial mixed salt of a copolymer of vinyl methyl ether and maleic acid;

about 15.4% of cellulose gum;

about 5% of mineral oil; and a petrolatum base;

wherein the copolymer reacts with waste by-products during use to become partially hydrated to thereby adhere to the skin and to form a barrier against diaper rash causative and irritant agents.

* * * * *

UNITED STATES PATENT AND TRADEMARK OFFICE
CERTIFICATE OF CORRECTION

PATENT NO. : 5,194,261
DATED : March 16, 1993
INVENTOR(S) : Pichierri, Virgil

It is certified that error appears in the above-identified patent and that said Letters Patent is hereby corrected as shown below:

In Column 7, line 2, change "undistributed" to --undisturbed--.

In Column 8, line 19, change "undistributed" to --undisturbed--.

Signed and Sealed this

Sixteenth Day of November, 1993

Attest:

BRUCE LEHMAN

*Attesting Officer*  *Commissioner of Patents and Trademarks*